United States Patent [19]

Batenburg et al.

[11] Patent Number: 6,087,138

[45] Date of Patent: Jul. 11, 2000

[54] PROCESS FOR THE PREPARATION OF SOTOLON

[75] Inventors: Amir Maximiliaan Batenburg; Johannes Jan Wesdorp, both of AT Vlaardingen, Netherlands

[73] Assignee: Unilever Patent Holdings BV, Vlaardingen, Netherlands

[21] Appl. No.: 09/243,445

[22] Filed: Feb. 3, 1999

[30] Foreign Application Priority Data

Feb. 3, 1998 [EP] European Pat. Off. .............. 98200313

[51] Int. Cl.[7] ......................... C12P 17/04; C07D 307/00; C07D 307/33
[52] U.S. Cl. ...................... 435/126; 435/146; 424/195.1; 549/295; 562/577
[58] Field of Search ........................... 562/577; 549/295; 435/146, 126; 424/195.1

[56] References Cited

U.S. PATENT DOCUMENTS 5,449,823  9/1995  Lerch ....................................... 562/577

FOREIGN PATENT DOCUMENTS

| 41844/93 | 2/1994 | Australia ........................ A23L 1/221 |
| 2236739 | 7/1997 | Canada ........................... A23L 1/221 |
| 0 381 972 B1 | 1/1994 | European Pat. Off. ......... A23L 1/221 |
| 0 623 580 A1 | 11/1994 | European Pat. Off. ....... C07C 59/215 |
| 0 888 717 A1 | 1/1999 | European Pat. Off. .......... A23L 1/00 |

OTHER PUBLICATIONS

Blank et al, J. Agric. Food Chem., 44:1851–1856 (1996).

Blank et al, Bioflavour, 95, pp. 385–388 (Feb. 14–17, 1995.

Blank et al, The Principal Flavor Components of Fenugreek, Chapter 3, 1997 American Chemical Society, pp. 12–28.

*Primary Examiner*—Herbert J. Lilling
*Attorney, Agent, or Firm*—Pillsbury Madison & Sutro LLP

[57] ABSTRACT

The present invention relates to a process for the preparation of a composition rich in sotolon from a source rich in 4-hydroxy-L-iso-leucine.

17 Claims, No Drawings

PROCESS FOR THE PREPARATION OF SOTOLON

FIELD OF THE INVENTION

The present invention relates to a process for the preparation of a composition rich in sotolon from a source rich in 4-hydroxy-L-iso-leucine.

BACKGROUND OF THE INVENTION

Sotolon (3-hydroxy-4,5-dimethyl-2(5H)-furanone) is a useful ingredient in sauces, condiments etcetera, as is described by Blank, I. et al, in various references, e.g. in ACS Symposium Series 660, (1997), pages 12–28, and also in Bioflavour 95, Feb. 14–17, 1995, Ed. INRA, Paris, (Les Colloques, no. 75), France, (Nestle). These references also disclose the chemical conversion of 4-hydroxy-iso-leucine (HIL) to sotolon using e.g. alpha-dicarbonyl compounds. These references also disclose that HIL can be found in fenugreek.

In U.S. Pat. No. 5,449,823 (Givaudan-Roure) it is disclosed that sotolon can be prepared from 4-hydroxy-iso-leucine via an intermediate compound. For performing the first reaction step the enzyme L-amino acid oxidase (or a micro-organism producing this) is needed. The pH for the first step is slightly acidic (5–7), the temperature for the second step is 80–250° C. This reference does also discloses that HIL is found abundantly in fenugreek and that sotolon is a valuable flavour.

EP 381972 (CPC) discloses a process for the preparation of a condiment similar to the product named after the inventor Julius Maggi. In said process, a mixture is prepared of 0– 70% soy sauce, 0–70% fish sauce, 5–20% salt, 1–30% fenugreek seeds, 0–80% water. Said mixture is allowed to mature, preferably under heating to 70–90° C. for 1 to 2 hours.

AU 41844/93 (Nestle) discloses a process for the preparation of a flavouring agent (meat flavour) in which a mixture containing lovage, amino acids and sugars is incubated with Lactobacilli, at a temperature of about 65° C. (not above 75° C.) for 22 hours. Lovage is a known source for flavours and contains, inter alia, sotolon.

SUMMARY OF THE INVENTION

The aim of the present invention is to provide a process for the preparation of a composition rich in sotolon. Said process should be convenient to carry out and without the need of very specialised enzymes, micro-organisms, "chemical" compounds, etcetera. With "chemical" compounds it is herein to be understood as compounds not usually seen as associated with food or food manufacturing. Preferably, said process should use widely available starting materials. Also, it is preferred that the process does not yield substantial amounts of side products which are less acceptable for incorporation in foodstuffs. More preferably, the composition rich in sotolon obtained according to the invention is such that it can be used in condiments, sauces etceteras without the need for extensive purification.

It has been found that the above objectives can be achieved by a process for manufacturing a composition comprising sotolon, wherein a composition comprising a source rich in 4-hydroxy-iso-leucine (HIL) is incubated at a temperature of higher than 50° C. and at a pH of 1–9 in the presence of sugars (in an amount of at least 0.1% by weight, based on the total reaction mixture). Incubating is herein to be understood as heating a mixture containing at least the compounds as set out above for a certain amount of time so as to allow the desired reaction to take place to a sufficient degree.

DETAILED DESCRIPTION OF THE INVENTION

Contrary to prior art processes, neither an enzyme having L-amino acid oxidase activity nor alpha-dicarbonyl compounds need to be added in the present invention. In the reaction according to the invention, it appeared necessary that sugars are present in the reaction medium (during at least part of the reaction) in a concentration of at least 0.1% by weight, based on the total reaction mixture. Preferably, the concentration of sugars is at least 0.2% by weight, based on the total amount. Even more preferred is an amount of 0.4% by weight. The sugars in this respect are preferably mono- and/or disaccharides. Preferred monosaccharides are pentoses, like e.g. xylose. Such sugars may be added as such or may be added in the form of carbohydrates, which may be (enzymatically) hydrolysed in situ to form the sugars needed.

The presence of at least a small amount of a compound having a primary amino group may also be preferred for the conversion of HIL to sotolon. A small amount in this respect may be understood as an amount of at least 0.1% Kjeldahl nitrogen based on the total composition. Although there are various compounds possible having such a primary amino group, it is preferred in this respect that such a compound having a primary amino group comprises a protein hydrolysate. Depending e.g. on the other process conditions, higher amounts of such a compound having a primary amino group (including protein hydrolysates) may also be preferred, e.g. in amounts of at least 0.3% Kjeldahl nitrogen based on the total composition, or even 0.6% Kjeldahl nitrogen.

Preferred protein hydrolysates with respect to the above may be protein hydrolysate comprising peptides. Such a peptide mixture can conveniently be obtained by hydrolysis of a protein source using e.g. a protease, but other sources for such a peptide mixture can also be used, such as a peptide-containing protein hydrolysate derived from a soy sauce, hydrolysed vegetable protein, yeast extract, enzymatic protein hydrolysate, or mixtures thereof. Preferably, the amount of such a peptide-containing protein hydrolysate is at least 0.1% Kjeldahl nitrogen based on the total composition. More preferably, the concentration of the peptide-containing protein hydrolysate is at least 1% Kjeldahl nitrogen based on the total composition, most preferred is an amount of at least 2% Kjeldahl nitrogen.

In the present invention, sotolon is prepared by conversion of 4-hydroxy-iso-leucine. Although in principle any source containing 4-hydroxy-iso-leucine can be used as a starting material, a convenient source, in which HIL is present in a considerable amount, is fenugreek. In particular, the seeds of fenugreek contain HIL, and hence provide a valuable starting material (e.g. in their dried, ground form). The concentration of HIL in the reaction medium is preferably as high as possible, although there are practical upper limits, due to the high viscosity if fenugreek is used as a source of HIL. Suitable processes involve e.g. a concentration of at least 0.5%, more preferably at least 2% (ground) fenugreek seeds.

Although it is set out above that the process according to the invention can be carried out at a pH of higher than 1, and lower than 9, it is preferred that the pH is at least 3, and lower than 6.

For a satisfactory conversion of HIL into sotolon it is desired that the incubation is effected for a prolonged period at an elevated temperature. It appeared that a higher temperature results in a higher conversion, although there seem to be practical upper limits. Above e.g. 250 or 200° C. more complex equipment is necessary, and thermal degradation (of sotolon) may also occur as a side reaction. The actual temperature chosen depends also on the time which is allowed for the incubation. As a general rule, the higher the temperature, the shorter the incubation can be. For good conversions at a reasonable time, it is preferred that the incubation is effected at a temperature higher than 75° C., or more preferably higher than 90° C. Incubation may last from e.g. 1 hour to several days, depending upon the temperature. A suitable combination is e.g. 40 hours or more at 100° C., or 5 hours or more at 120° C.

The actual combination of incubation temperature and time will depend on the equipment available, but for economical reasons the combination will be such that conversion of HIL to sotolon is substantial, e.g. so that more than 180 ppm sotolon is produced, based on dry fenugreek seeds. More preferably reaction time and reaction temperature are chosen such that at least 500 ppm sotolon is produced, based on dry fenugreek seeds.

Contrary to some prior art processes, the process according to the present invention may be carried out as a one-step process. The process can also be distinguished from prior art processes in that it does not require the presence of substantial amounts of L-amino acid oxidase or a microorganism producing said enzyme.

Although the process according to the invention can be carried out as such to produce a composition rich in sotolon, it is also possible to have this process incorporated into a process for the preparation of a sauce, condiment etcetera which should contain at least a certain amount of sotolon.

The invention further extends to sauces (including soy sauce and fish sauce), soups, condiments, etcetera, containing sotolon as produced according to the present invention.

The invention is further exemplified by the following examples, which are to be understood as to be non-limiting.

EXAMPLE 1

A model hydrolysate was produced by incubating a 10% dispersion of soy meal and roasted wheat (7:3 w/w) with 0.1% Flavourzyme (Novo Nordisk) at 45° C. for 2 days under sterile conditions. Ground fenugreek seed (Verstegen, NL) was added in a concentration of 3% (w/v), and after adjusting to pH=5 the mixture was heated for 48 hours at 100° C. and analysed for sotolon by HPLC measurement after several intervals. For reasons of comparison the fenugreek material was similarly treated in an acetate buffer and in a solution of yeast autolysate of the same content of proteinaceous material as the hydrolysate (YEP-L, Quest-Int.). The initial concentration of sotolon in the ground fenugreek was approx. 15 ppm.

TABLE 1

HIL to sotolon conversion in various media

| Medium | [Sotolon] (5 hrs) | [Sotolon] (24 hrs) | [Sotolon] (48 hrs) |
|---|---|---|---|
| Hydrolysate | 107 ppm | 652 ppm | 1356 ppm |
| Buffer* | 34 ppm | 72 ppm | 145 ppm |
| Yeast autolysate* | 44 ppm | 87 ppm | 155 ppm |

*Comparative examples

All sotolon data refer to concentrations on dry, ground fenugreek seed.

EXAMPLE 2

The main difference between the hydrolysate and the yeast extract of example 1 is the virtually complete absence of sugars in the latter. The influence of sugars was studied by incorporation of monosaccharides in the buffer medium and by removal of simple sugars from the hydrolysate by lactic acid bacterial fermentation on the other hand. This pH-stat fermentation led to reduction of the monosaccharide content to levels below 0.1%. Conditions and preparation of soy hydrolysate are as described in example 1.

TABLE 2

Influence of sugar on conversion efficiency

| Medium | [Sotolon] (24 hrs, pH5 100° C.) |
|---|---|
| Hydrolysate | 662 ppm |
| Fermented hydrolysate* | 174 ppm |
| Fermented hydrolysate + 0.3% xylose | 518 ppm |
| Buffer* | 72 ppm |
| Buffer + 0.3% xylose | 185 ppm |

*Comparative examples

All sotolon data refer to concentrations on dry, ground fenugreek seed.

EXAMPLE 3

Addition of 0.4% xylose was found to lead to complete recovery of the HIL conversion efficiency of the soy hydrolysate after lactic acid bacterial fermentation to the level before fermentation. In this medium the pH, temperature and duration of the treatment were varied, resulting in the data of tables 3 and 4. Heating at 120° C. leads to an approximately 10 fold increase in conversion rate, when compared with 100° C., at the conditions chosen.

TABLE 3

Effect of time and temperature on conversion of HIL to sotolon

| Conditions (pH = 5) | [Sotolon] (ppm) |
|---|---|
| 5 hrs 100° C. | 102 |
| 24 hrs 100° C. | 609 |
| 48 hrs 100° C. | 1378 |
| 120 hrs 100° C. | 2950 |
| 5 hrs 120° C. | 1088 |

TABLE 4

Effect of pH on conversion of HIL to sotolon

| pH (100° C., 24 hrs.) | [Sotolon] (ppm) |
|---|---|
| pH = 2 | 392 |
| pH = 3 | 700 |
| pH = 4 | 903 |
| pH = 5 | 623 |
| pH = 6 | 360 |

All sotolon data refer to concentrations on dry, ground fenugreek seed.

EXAMPLE 4

Several types of media were investigated with respect to their suitability for the hydroxy-isoleucine conversion. As a representative of a pure protein hydrolysate without significant amounts of carbohydrate, sodium caseinate was hydrolysed during 8 hrs at 50° C. and pH=7 with 1% (DM/DM) of the protease Orientase 90N (Jan Dekker, Naarden, NL), leading to a DH of approximately 25% and a free amino acid concentration of <5%. Alternatively a casein hydrolysate was produced with the additional use of peptidase preparations, Debitrase (Imperial Biotechnology Ltd., U.K.) and Flavourzyme (Novo-Nordisk), leading to a DH of >75% and a free amino acid (FAA) fraction of approximately 60%. Soy sauce was obtained from Kikkoman, and optionally diluted to the same protein dry matter content as the soy and casein hydrolysates. The amino acid mixture contains free amino acids (FAA) in the ratio found in casein. Soy hydrolysate and yeast autolysate are described in example 1. The protein hydrolysates and the amino acid mixture were added to the medium in such an amount that the proteinaceous material equals 5% (equal to about 0.8% Kjeldahl nitrogen). Sotolon production in a 3% suspension of ground fenugreek seed after 24 hrs. at 100° C. and pH=5 is given in table 5.

TABLE 5

| Medium | [Sotolon] (ppm) |
|---|---|
| soy hydrolysate (ex example 1) | 637 |
| low FAA casein hydrolysate* | 167 |
| low FAA casein hydrolysate + 0.4% xylose | 650 |
| high FAA casein hydrolysate + 0.4% xylose | 440 |
| amino acid mixture + 0.4% xylose | 230 |
| yeast autolysate* | 67 |
| yeast autolysate + 0.4% xylose | 467 |
| diluted soy sauce + 0.4% xylose | 537 |
| soy sauce + 0.4% xylose | 983 |

*Comparative examples

All sotolon data refer to concentrations on dry, ground fenugreek seeds.

EXAMPLE 5

The effect of the concentration of sugar and proteinaceous material was investigated by a series of experiments in which one of the two components was varied. Xylose and the low-FAA casein hydrolysate of example 4 were used as medium components. Ground fenugreek seed was suspended to 3%. Sotolon production after 24 hours at 100° C. and pH 5 is given table 6.

TABLE 6

Effect of concentration of sugar and proteinaceous material on HIL conversion

| [xylose] (%) | [casein hydrolysate] (% DM) | [Sotolon] (ppm) |
|---|---|---|
| 0* | 0 | 78 |
| 0.4 | 0 | 188 |
| 0.4 | 0.5 | 312 |
| 0.4 | 1 | 273 |
| 0.4 | 2 | 461 |
| 0.4 | 5 | 625 |
| 0.4 | 10 | 602 |
| 0.4 | 15 | 617 |
| 0* | 5 | 180 |
| 0.1 | 5 | 250 |
| 0.2 | 5 | 328 |
| 0.4 | 5 | 625 |
| 1 | 5 | 1172 |
| 2.5 | 5 | 1523 |

*Comparative example

All sotolon data refer to concentrations on dry, ground fenugreek seeds.

EXAMPLE 6

Various types of carbohydrates were investigated with respect to their promotion of HIL to sotolon conversion 5 during an incubation of 24 hours at pH 5 and 100° C. in the presence of 5% low FAA casein hydrolysate, described in example 4 (table 7). The concentration of ground fenugreek seed was 3%. The maltodextrin, Paselli MD6, was obtained from Avebe (NL).

TABLE 7

Effect of type of carbohydrate on formation of sotolon from HIL

| | [Sotolon] (ppm) | |
|---|---|---|
| Type of carbohydrate | 0.4% carbohydrate | 2.5% carbohydrate |
| Xylose | 639 | 1992 |
| Glucose | 498 | 1975 |
| Sucrose | 373 | 913 |
| Raffinose | 373 | 747 |
| Maltodextrin | 232 | 249 |

EXAMPLE 7

3% Ground fenugreek suspensions were made in solutions of two different xylose concentrations, without protein hydrolysate, with a pure protein hydrolysate the low FAA casein hydrolysate of example 4), and with soy hydrolysate (the fermented hydrolysate of example 2), in a concentration of 5% proteinaceous material. The resulting sotolon concentrations after incubation for 24 hours at 100° C. at pH 5.0 are given in table 8.

TABLE 8

Effect of the presence and type of protein hydrolysate on HIL conversion

| | [Sotolon] (ppm) | |
|---|---|---|
| Type of protein hydrolysate | 0.4% carbohydrate | 2.5% carbohydrate |
| None | 155 | 487 |
| Fermented soy hydrolysate | 620 | 1388 |
| Low FAA casein hydrolysate | 598 | 1447 |

What is claimed is:
1. Process for manufacturing a composition comprising sotolon, wherein a source rich in 4-hydroxy-iso-leucine (HIL) is incubated at a temperature of higher than 50° C. and at a pH of 1–9 in the presence of at least 0.1% by weight of sugars, based on the total reaction mixture and in the absence of L-amino oxidase or microorganism producing the enzyme.

2. Process according to claim 1, wherein the concentration of the sugars is at least 0.2 % by weight.

3. Process according to claim 2, wherein the concentration of the sugars is at least 0.4% by weight.

4. Process according to claim 1, wherein the reaction mixture further comprises a compound having a primary amino group in an amount of at least 0.1% Kjeldahl nitrogen based on the total composition.

5. Process according to claim 4, wherein the compound having a primary amino group comprises a protein hydrolysate.

6. Process according to claim 5, wherein the concentration of the protein hydrolysate is at least 0.3% Kjeldahl nitrogen base on the total composition.

7. Process according to claim 5, wherein the protein hydrolysate comprises peptides.

8. Process according to claim 5, wherein the protein hydrolysate is derived from a soy sauce, hydrolysed vegetable protein, yeast extract, enzymatic protein hydrolysate, or mixture thereof.

9. Process according to claim 1, wherein the pH at incubation is between 3 and 6.

10. Process according to claim 1, wherein the incubation is effected at a temperature higher than 75° C.

11. Process according to claim 10, wherein the incubation is effected at a temperature higher than 90° C.

12. Process according to claim 1, wherein the incubation is effected at a temperature lower than 200° C.

13. Process according to claim 1 wherein the sugars comprise monosaccharides.

14. Process according to claim 1, wherein the source comprising HIL is derived from fenugreek.

15. Process according to claim 1, wherein the reaction time and reaction temperature are chosen such that more than 180 ppm sotolon is produced, based on dry fenugreek seeds.

16. Process according to claim 15, wherein the reaction time and reaction temperature are chosen such that at least 500 ppm sotolon is produced, based on dry fenugreek seeds.

17. Process according to claim 1, wherein the process is carried out as a one-step process.

* * * * *